United States Patent
Foody et al.

(10) Patent No.: US 7,727,746 B2
(45) Date of Patent: Jun. 1, 2010

(54) UPFLOW REACTOR FOR ENZYMATIC HYDROLYSIS OF CELLULOSE

(75) Inventors: Brian Foody, Ottawa (CA); Ziyad Rahme, Ottawa (CA); Jeffrey S. Tolan, Ottawa (CA)

(73) Assignee: Iogen Energy Corporation, Ontario (CA)

( * ) Notice: Subject to any disclaimer, the term of this patent is extended or adjusted under 35 U.S.C. 154(b) by 300 days.

(21) Appl. No.: 11/303,424

(22) Filed: Dec. 16, 2005

(65) Prior Publication Data

US 2006/0154352 A1   Jul. 13, 2006

(51) Int. Cl.
C12P 19/14   (2006.01)

(52) U.S. Cl. .................. 435/99; 435/105; 435/158; 435/161

(58) Field of Classification Search .............. 435/99
See application file for complete search history.

(56) References Cited

U.S. PATENT DOCUMENTS

| | | | | |
|---|---|---|---|---|
| 3,637,491 | A | * | 1/1972 | Hedrick et al. .............. 210/734 |
| 3,972,775 | A | | 8/1976 | Wilke et al. |
| 4,735,724 | A | | 4/1988 | Chynoweth et al. ......... 210/603 |
| 5,258,293 | A | * | 11/1993 | Lynd et al. .................. 435/165 |
| 5,837,506 | A | | 11/1998 | Lynd et al. .................. 435/165 |
| 5,888,806 | A | | 3/1999 | Nguyen ..................... 435/291 |
| 5,962,289 | A | | 10/1999 | Kilburn et al. |
| 6,555,350 | B2 | | 4/2003 | Ahring et al. ............... 435/162 |

FOREIGN PATENT DOCUMENTS

| | | | |
|---|---|---|---|
| JP | 10-263313 | | 10/1998 |
| WO | WO9718167 | * | 5/1997 |

OTHER PUBLICATIONS

Knutsen and Davis; "Combined Sedimentation and Filtration Process for Cellulase Recovery During Hyddrolysis of Lignocellulosic Biomass"; *Applied Biochemistry and Biotechnology*; (2002); 98-100: 1161-1172.
Kleijntjens, et al.; "A Continuous Thermophilic Cellulose Fermentation in an Upflow Reactor by a Clostridium Therocellum Containing Mixed Culture"; *Biotechnology Letters*; (1986); 8(9): 667-672.
Grethlein; Chemical Breakdown of Cellulosic Materials; *J. Appl. Chem. Biotechnol.*; (1978); 28: 296-308.
Mores, et al.; "Cellulase Recovery via Membrane Filtration"; *Applied Biochemistry and Biotechnology*; (2001); 91-93: 297-309.
International Search Report for PCT/CA2005/001922 mailed Mar. 30, 2006.
Alfani, "Membrane Reactors for the Investigation of Product Inhibition of Enzyme Activity", Journal of Membrane Science, vol. 52 (1990) 339-50 (presented 1988).
Ohlson, et al., "Enzymatic Hydrolysis of Sodium-Hydroxide-Pretreated Sallow in an Ultrafiltration Membrane Reactor", Biotechnology and Bioengineering, vol. 26 (1984) 647-53.
Ishihara, et al., "Semicontinuous Enzymatic Hydrolysis of Lignocelluloses", Biotechnolgy and Bioengineering, vol. 37 (1991) 948-54.
Tan, et al., "Column cellulose hydrolysis reactor: Cellulase adsorption profile", Appl. Microbiol. Biotechnol., vol. 25 (1986) 256-61.
Knutsen, et al., "Combined Sedimentation and Filtration Process for Cellulase Recovery During Hydrolysis of Lignocellulosic Biomass", Applied Biochemistry and Biotechnology, vol. 98-100 (2002) 1161-72.
Mores, et al., "Cellulase Recovery via Membrane Filtration" Applied Biochemistry and Biotechnology, vol. 91-93 (2001) 297-309.
Ramos, et al., "The use of enzyme recycling and the influence of sugar accumulation on cellulose hydrolysis by Trichoderma cellulases", Enzyme Microb. Technol., vol. 15 (1993) 19-25.
Lee, et al., "Evaluation of Cellulase Recycling Strategies for the Hydrolysis of Lignocellulosic Substrates", Biotechnology and Bioengineering, vol. 45 (1995) 328-36.

* cited by examiner

*Primary Examiner*—Jon P Weber
*Assistant Examiner*—Tiffany M Gough
(74) *Attorney, Agent, or Firm*—Fitzpatrick, Cella, Harper & Scinto

(57) ABSTRACT

A process for the enzymatic hydrolysis of cellulose to produce a hydrolysis product from a pre-treated cellulosic feedstock is provided. The process comprises introducing an aqueous slurry of the pre-treated cellulosic feedstock at the bottom of a hydrolysis reactor. Axial dispersion in the reactor is limited by avoiding mixing and maintaining an average slurry flow velocity of about 0.1 to about 20 feet per hour, such that the undissolved solids flow upward at a rate slower than that of the liquid. Cellulase enzymes are added to the aqueous slurry before or during the step of introducing. An aqueous stream comprising hydrolysis product and unhydrolyzed solids is removed from the hydrolysis reactor. Also provided are enzyme compositions which comprise cellulase enzymes and flocculents for use in the process. In addition, a kit comprising cellulase enzymes and flocculent is provided.

46 Claims, 8 Drawing Sheets

UPFLOW REACTOR FOR ENZYMATIC HYDROLYSIS OF CELLULOSE

The present invention relates to processes for the conversion of cellulosic feedstocks. More specifically, the present invention relates to processes for enzymatic conversion of cellulosic feedstocks having improved efficiency.

BACKGROUND OF THE INVENTION

Fuel ethanol is currently produced from feedstocks such as cornstarch, sugar cane, and sugar beets. However, the production of ethanol from these sources cannot expand much further due to limited farmland suitable for the production of such crops and competing interests with the human and animal food chain. Finally, the use of fossil fuels, with the associated release of carbon dioxide and other products, in the conversion process is a negative environmental impact of the use of these feedstocks The possibility of producing ethanol from cellulose-containing feedstocks such as agricultural wastes, grasses, and forestry wastes has received much attention due to the availability of large amounts of these inexpensive feedstocks, the desirability to avoid burning or landfilling cellulosic waste materials, and the cleanliness of ethanol as a fuel compared to gasoline. In addition, a byproduct of the cellulose conversion process, lignin, can be used as a fuel to power the cellulose conversion process, thereby avoiding the use of fossil fuels. Studies have shown that, taking the entire cycle into account, the use of ethanol produced from cellulose generates close to nil greenhouse gases.

The cellulosic feedstocks that may be used for ethanol production include (1) agricultural wastes such as corn stover, wheat straw, barley straw, oat straw, oat hulls, canola straw, and soybean stover; (2) grasses such as switch grass, miscanthus, cord grass, and reed canary grass; (3) forestry wastes such as aspen wood and sawdust; and (4) sugar processing residues such as bagasse and beet pulp.

Cellulose consists of a crystalline structure that is very resistant to breakdown, as is hemicellulose, the second most prevalent component of cellulosic feedstocks. The conversion of cellulosic fibers to ethanol requires: 1) liberating cellulose and hemicellulose from lignin or increasing the accessibility of cellulose and hemicellulose within the cellulosic feedstock to cellulase enzymes, 2) depolymerizing hemicellulose and cellulose carbohydrate polymers to free sugars, and 3) fermenting the mixed hexose and pentose sugars to ethanol.

Among well-known methods used to convert cellulose to sugars is an acid hydrolysis process involving the use of steam and acid at a temperature, acid concentration and length of time sufficient to hydrolyze the cellulose to glucose (Grethlein, 1978, J. Appl. Chem. Biotechnol. 28:296-308). The glucose is then fermented to ethanol using yeast, and the ethanol is recovered and purified by distillation.

An alternative method of cellulose hydrolysis is an acid prehydrolysis (or pre-treatment) followed by enzymatic hydrolysis. In this sequence, the cellulosic material is first pre-treated using the acid hydrolysis process described above, but at milder temperatures, acid concentration and treatment time. This pre-treatment process increases the accessibility of cellulose within the cellulosic fibers for subsequent enzymatic conversion steps, but results in little conversion of the cellulose to glucose itself. In the next step, the pre-treated feedstock is adjusted to an appropriate temperature and pH, then submitted to enzymatic conversion by cellulase enzymes.

The hydrolysis of the cellulose, whether by acid or by cellulase enzymes, is followed by the fermentation of the sugar to ethanol, which is then recovered by distillation.

The efficient conversion of cellulose from cellulosic material into sugars, and the subsequent fermentation of sugars to ethanol, is faced with a major challenge regarding commercial viability. In particular, acid prehydrolysis requires large amounts of acid. For a clean feedstock, such as washed hardwood, the sulfuric acid demand is 0.5% to 1% of the dry weight of the feedstock; for agricultural fibers, which can contain high levels of silica, salts, and alkali potassium compounds from the soil, the acid demand can be up to about 10-fold higher, reaching 5% to 7% by weight of feedstock. This adds significant cost to the process. A second drawback of using large amounts of acids in a prehydrolysis process is that the acidified feedstock must be neutralized to a pH between about 4.5 and about 5 prior to enzymatic hydrolysis with cellulase enzyme. The amount of caustic soda used to neutralize acidified feedstock is proportional to the amount of acid used to acidify the feedstock. Thus, high acid usage results in high caustic soda usage, which further increases the cost of processing cellulosic feedstock to ethanol. Furthermore, the cost of enzymatic hydrolysis is high, as cellulose remains resistant to hydrolysis despite pre-treatment, which increases the enzyme dosage required. Such increased requirement can be counteracted by increasing the hydrolysis times (90-200 hours), in turn requiring very large reactors, which again adds to the overall cost.

A method of decreasing the enzyme dosage while maintaining high levels of cellulose conversion is Simultaneous Saccharification and Fermentation (SSF). In this type of system, enzymatic hydrolysis is carried out concurrently with yeast fermentation of glucose to ethanol in a reactor vessel. During SSF, the yeast removes glucose from the reactor by fermenting it to ethanol and this decreases inhibition of the cellulase by glucose. However, the cellulase enzymes are still inhibited by ethanol. SSF is typically carried out at temperatures of 35-38° C., which is a compromise between the 50° C. optimum for cellulase and the 28° C. optimum for yeast. This intermediate temperature leads to substandard performance by both the cellulase enzymes and the yeast. Thus, the inefficient catalysis requires very long reaction times and very large reaction vessels—both of which are costly.

A method for higher volumetric productivity is disclosed in U.S. Pat. No. 5,258,293 (Lynd). This method utilizes a lignocellulosic feedstock along with microorganisms that are continuously introduced into a reaction vessel. Fluid is also continuously added from the bottom of the reaction vessel, but no mechanical agitation of the slurry occurs. As the reaction progresses, the lignocellulosic feedstock being digested tends to accumulate in a spatially non-homogenous layer while the ethanol product rises to a top layer, where it is removed. The insoluble substrate accumulates in a bottom layer and can be withdrawn from the vessel. This arrangement results in a differential retention of the fermenting substrate, which allows for increased residence time in the reactor vessel.

In another approach, disclosed in U.S. Pat. No. 5,837,506 (Lynd), ethanol is produced using an intermittently agitated, perpetually fed bioreactor. Lignocellulosic slurry and microorganisms are added to a reactor; the mixture is then agitated, either by mechanical means or by fluid recirculation, for a specific time interval, after which it is allowed to settle. Ethanol is then removed from a top portion of the reactor, additional substrate is added, and the cycle continues. In a similar method, Kleijntjens et al. (1986, Biotechnology Letters, 8:667-672) utilize an upflow reactor to ferment cellulose-containing substrate in the presence of C. thermocellum. The substrate slurry settles to form an aggregated fibre bed, which is accelerated by slow mechanical stirring. Substrate is added periodically, while liquid is continuously fed to the reactor. Ethanol product accumulates in a top layer, where it is removed from the reactor. The methods disclosed in U.S. Pat. No. 5,837,506, U.S. Pat. No. 5,258,293 and Kleijntjens et al. result in an increase in the residence time of the feedstock in the reactor vessel. However, all three methods suffer from the disadvantages of the SSF process.

U.S. Pat. No. 5,348,871; U.S. Pat. No. 5,508,183; U.S. Pat. No. 5,248,484; and U.S. Pat. No. 5,637,502 (Scott) teach a method to improve the conversion efficiency in enzymatic hydrolysis through the use of an attritor in association with an agitated reactor vessel. The agitator produces a high-shear field for size reduction of solid particles in the cellulosic feedstock, which constantly provides new surface area for the cellulase enzymes. Therefore, the reaction efficiency is increased and the enzyme requirements are decreased. However, the high shear often inactivates the enzymes. Furthermore, the cost of the attritor equipment is much greater than the savings due to the decreased enzyme dosage.

U.S. Pat. No. 5,888,806 and U.S. Pat. No. 5,733,758 (Nguyen) teach an alternative approach using a tower hydrolysis reactor comprising alternating mixed and unmixed zones, thus reducing the mixing power consumption and cost. The slurry is moved upward in plug flow through the reactor and is intermittently mixed in the mixing zones, thus preventing channeling of liquid and ensuring uniform heat and mass transfer. While the methods disclosed in U.S. Pat. No. 5,888,806 and U.S. Pat. No. 5,733,758 reduce the shearing and denaturation of the enzymes, the cost of the mixing equipment is substantial. Furthermore, the kinetic performance of the enzymes is no better than can be achieved in a batch hydrolysis mode.

At present there is much difficulty in the art to attain high conversion efficiency while maintaining lowered costs. Increasing hydrolysis times to avoid higher costs of increasing the enzyme dosage requires larger reactors, which in turn increases equipment costs. Mixing and intermittent mixing of the feedstock during hydrolysis can increase enzyme efficiency but equipment costs will again increase, and shear forces will cause enzyme denaturation. Other systems compromise the optimal enzyme activity and reduce the efficiency of the enzymes.

SUMMARY OF THE INVENTION

The present invention relates to processes for the conversion of cellulosic feedstocks into products. More specifically, the present invention relates to processes for the enzymatic conversion of cellulosic feedstocks having improved efficiency.

According to the present invention, there is provided an upflow settling reactor for enzymatic hydrolysis of cellulose.

The present invention also provides a process for the enzymatic hydrolysis of cellulose to produce a hydrolysis product from a pre-treated cellulosic feedstock, the process comprising:

i) providing an aqueous slurry of the pre-treated cellulosic feedstock, the slurry comprising from about 3% to about 30% undissolved solids in a liquid, the undissolved solids comprising at least about 20% cellulose;

ii) introducing the aqueous slurry at the bottom of a hydrolysis reactor and limiting axial dispersion in the reactor by avoiding mixing, and maintaining an average slurry flow velocity of about 0.1 to about 20 feet per hour, such that the undissolved solids flow upward at a rate slower than that of the liquid;

iii) adding cellulase enzymes to the aqueous slurry before or during the step of introducing (step ii); and iv) removing an aqueous stream comprising hydrolysis product and unhydrolyzed solids from the hydrolysis reactor, the hydrolysis product comprising glucose, cellobiose, glucose oligomers, or a combination thereof.

The present invention relates to the process for the enzymatic hydrolysis of cellulose as defined above, wherein, in the step of introducing (step ii), the aqueous slurry is introduced at the bottom of the hydrolysis reactor with a uniform radial distribution.

The present invention is directed to the process for the enzymatic hydrolysis of cellulose as defined above, wherein, in the step of adding (step iii), one or more than one flocculating compound is added to the aqueous slurry, separately from, or together with the cellulase enzymes, or a combination thereof. Furthermore, the one or more than one flocculating compound may be added before or during the step of introducing (step ii), or a combination thereof.

The present invention pertains to the process for the enzymatic hydrolysis of cellulose as defined above, wherein, in the step of providing (step i), the slurry comprises from about 5% to about 20% by weight undissolved solids, and the undissolved solids comprise from about 25% to about 70% by weight cellulose.

The present invention is directed to the process as described above, wherein the pre-treated cellulosic feedstock is obtained from wheat straw, oat straw, barley straw, corn stover, soybean stover, canola straw, sugar cane bagasse, switch grass, reed canary grass, cord grass, oat hulls, sugar beet pulp or miscanthus. Furthermore, the pre-treated cellulosic feedstock may have been subjected to pre-treatment from about 160° C. to about 280° C. and for about 3 seconds to about 30 minutes at an acid concentration from about 0% to about 5% prior to enzymatic hydrolysis. The acid may be selected from the group consisting of sulfuric acid, sulfurous acid, and sulfur dioxide. Optionally, a liquid stream comprising sugar may be separated from the pre-treated cellulosic feedstock prior to the step of introducing (step ii). The liquid stream may be separated from the feedstock using processes such as filtration, centrifugation, washing or any other suitable process as would be known in the art. If washing is used for the separation, it may be carried out using a suitable washing medium such as water, a recycled process stream, treated effluent, or a combination thereof.

The present invention also provides for the process as described above, wherein, in the step of adding (step iii), the cellulase enzyme is added at a dosage from about 1.0 to about 40.0 FPU per gram of cellulose.

Furthermore, the present invention provides the process as described above, where, in the step of removing (step iv), at least a portion of the hydrolysis product stream is separated from the unhydrolyzed solids by using a clarifier zone at the top of the unmixed hydrolysis reactor. The hydrolysis product and the unhydrolyzed solids may be removed from the clarifier zone at separate locations. Alternatively, at least a portion of the hydrolysis product stream is separated from the unhydrolyzed solids using a solids-liquid separator.

The present invention is directed to the process as described above, wherein, in the step of adding (step iii), the cellulase enzymes are chosen to produce glucose, cellobiose, glucose oligomers, or a combination thereof.

The present invention also provides for the process as described above, wherein, in the step of providing (step i), the pH of the slurry is adjusted from about 4.0 to about 6.0, preferably from about 4.5 to about 5.5. Furthermore, the temperature may be from about 45° C. to about 70° C., preferably about 45° C. to about 65° C.

The present invention relates to the process as described above, wherein, in the step of adding (step iii), one or more than one flocculating compound is used. The flocculating compound may be selected from the group consisting of a cationic polymer, a non-ionic polymer, an anionic polymer, an amphoteric polymer, salts, alum, and a combination thereof. Preferably, the one or more than one flocculating compound is the cationic polymer, for example, but not limited to, a polyacrylamide. The flocculating compound may be added at a dosage from about 0.1 to about 4 kg per tonne solids.

The present invention also relates to the process as described above, wherein the average slurry flow velocity is between about 0.1 and about 12 feet per hour, more preferably, between about 0.1 and about 4 feet per hour.

The present invention also provides an enzyme composition comprising cellulase enzymes and one or more than one flocculent, for hydrolyzing cellulose to glucose, cellobiose, glucose oligomers, or a combination thereof. Preferably, the cellulase enzymes are produced by *Aspergillus, Humicola, Trichoderma, Bacillus, Thermobifida*, or a combination thereof. Furthermore, the one or more than one flocculating compound may be selected from the group consisting of a cationic polymer, a non-ionic polymer, an anionic polymer, an amphoteric polymer, salts, alum, and a combination thereof. Preferably, the one or more than one flocculating compound is the cationic polymer, for example a polyacrylamide.

The present invention is also directed to a use of an enzyme composition comprising cellulase enzymes and one or more than one flocculent for hydrolyzing cellulose to glucose, cellobiose, glucose oligomers, or a combination thereof.

The present invention is also directed to a use of an enzyme composition comprising cellulase enzymes and one or more than one flocculent for the enzymatic hydrolysis of cellulose to produce a hydrolysis product from a pre-treated cellulosic feedstock, the use of the enzyme composition comprising:

i) providing an aqueous slurry of the pre-treated cellulosic feedstock, the slurry comprising from about 3% to about 30% undissolved solids in a liquid, the undissolved solids comprising at least about 20% cellulose;

ii) introducing the aqueous slurry at the bottom of a hydrolysis reactor and limiting axial dispersion in the reactor by avoiding mixing, and maintaining an average slurry flow velocity of about 0.1 to about 20 feet per hour, such that the undissolved solids flow upward at a rate slower than that of the liquid;

iii) adding the enzyme composition to the aqueous slurry before or during the step of introducing (step ii); and iv) removing an aqueous stream comprising hydrolyzed product and unhydrolyzed solids from the hydrolysis reactor, the hydrolysis product comprising glucose, cellobiose, glucose oligomers, or a combination thereof.

Preferably, the cellulase enzymes are produced by *Aspergillus, Humicola, Trichoderma, Bacillus, Thermobifida*, or a combination thereof, and the one or more than one flocculating compound may be selected from the group consisting of a cationic polymer, a non-ionic polymer, an anionic polymer, an amphoteric polymer, salts, alum, and a combination thereof. Preferably, the one or more than one flocculating compound is the cationic polymer, for example, a polyacrylamide.

The present invention also provides an enzyme composition comprising cellulase enzymes and one or more than one flocculent, for hydrolyzing cellulose to glucose, cellobiose, glucose oligomers, or a combination thereof, wherein the hydrolysis is carried out by:

i) providing an aqueous slurry of the pre-treated cellulosic feedstock, the slurry comprising from about 3% to about 30% undissolved solids in a liquid, the undissolved solids comprising at least about 20% cellulose;

ii) introducing the aqueous slurry at the bottom of a hydrolysis reactor, limiting axial dispersion in the reactor by avoiding mixing, and maintaining an average slurry flow velocity of about 0.1 to about 20 feet per hour, such that the undissolved solids flow upward at a rate slower than that of the liquid;

iii) adding the enzyme composition to the aqueous slurry before or during the step of introducing (step ii); and iv) removing an aqueous stream comprising hydrolysis product and unhydrolyzed solids from the hydrolysis reactor, the hydrolysis product comprising glucose, cellobiose, glucose oligomers, or a combination thereof.

The present invention provides a kit comprising cellulase enzymes and one or more than one flocculent and instructions for hydrolyzing cellulose to produce a hydrolysis product from a pre-treated cellulosic feedstock, the instructions comprising:

i) providing an aqueous slurry of the pre-treated cellulosic feedstock, the slurry comprising from about 3% to about 30% undissolved solids in a liquid, the undissolved solids comprising at least about 20% cellulose;

ii) introducing the aqueous slurry at the bottom of a hydrolysis reactor and limiting axial dispersion in the reactor by avoiding mixing, and maintaining an average slurry flow velocity of about 0.1 to about 20 feet per hour, such that the undissolved solids flow upward at a rate slower than that of the liquid;

iii) adding the cellulase enzyme mixture and the one or more than one flocculent to the aqueous slurry before or during the step of introducing (step ii); and iv) removing an aqueous stream comprising hydrolysis product and unhydrolyzed solids from the hydrolysis reactor, the hydrolysis product comprising glucose, cellobiose, glucose oligomers, or a combination thereof.

The present invention also provides a method for preparing an enzyme composition for use in hydrolyzing cellulose to produce a hydrolysis product from a pre-treated cellulosic feedstock, the method comprising obtaining one or more than one cellulase enzymes from a plant, fungal or microbial source, and combining the cellulase enzymes with one or more than one flocculent to produce the enzyme composition.

The present invention also provides the method for preparing the enzyme composition as described above, wherein the cellulase enzymes are produced by *Aspergillus, Humicola, Trichoderma, Bacillus* and *Thermobifida*.

The present invention provides a system for hydrolyzing cellulose to glucose, cellobiose, glucose oligomers, or a combination thereof, the system comprising a feedstock slurry supply line in fluid communication with an input to an upflow hydrolysis reactor, a solids-liquid separator in fluid communication with the upflow hydrolysis reactor and comprising a first output for withdrawing a slurry comprising unhydrolyzed solids and a second output for withdrawing a stream comprising hydrolysis product, the hydrolysis product comprising glucose, cellobiose, glucose oligomers, or a combination thereof, wherein the feedstock supply line, the upflow hydrolysis reactor, or both the feedstock supply line and the upflow hydrolysis reactor, comprise an enzyme composition comprising cellulase enzymes and one or more than one flocculent.

The present invention also provides a system as described above, wherein the feedstock supply line, when in use, comprises a pre-treated feedstock. The solids-liquid separator may be a settling tank, a clarifier, a clarifier zone, a centrifuge or a filter. When the system is in use, cellulase enzymes may be present at a dosage from about 1.0 to about 40.0 FPU per gram of cellulose of the pre-treated feedstock and one or more than one flocculating compound may be present at a dosage from about 0.1 to about 4.0 kg per tonne of solids of the pre-treated feedstock.

As described herein, the operation of the hydrolysis of cellulose within an upflow settling reactor may be enhanced by the addition of one or more flocculating compounds. The flocculating compounds increase the size of the cellulosic solids, thereby increasing the rate of the settling of the cellulosic solids. This helps to hold the solids in the reactor for a longer period of time, thereby increasing the degree of conversion of the cellulose. Furthermore, the process as described herein provides for the hydrolysis of the feedstock slurry within the hydrolysis reactor in the absence of mixing, in that no active mixing of the slurry, through the use of impellers, pumps or the like, within the hydrolysis tank is required.

The use of the upflow settling hydrolysis reactor addresses several of the shortcomings of the prior art. The invention improves the efficiency of the enzymatic hydrolysis of cellulose. This results in a higher degree of conversion of the cellulose to glucose. Alternatively, the upflow settling reactor results in a lower requirement for cellulase enzymes than conventional hydrolysis systems. The improved enzymatic hydrolysis is achieved without the expense of mixing of the slurry within the hydrolysis reactor, and without adding intense shear to the system. The improvements associated with the use of an upflow hydrolysis reactor may be enhanced by using a flocculating compound.

BRIEF DESCRIPTION OF THE DRAWINGS

These and other features of the invention will become more apparent from the following description in which reference is made to the appended drawings wherein:

FIG. 1 shows a schematic of a system comprising an upflow reactor that may be used in accordance with an embodiment of the present invention.

DESCRIPTION OF PREFERRED EMBODIMENT

Figure 1A:
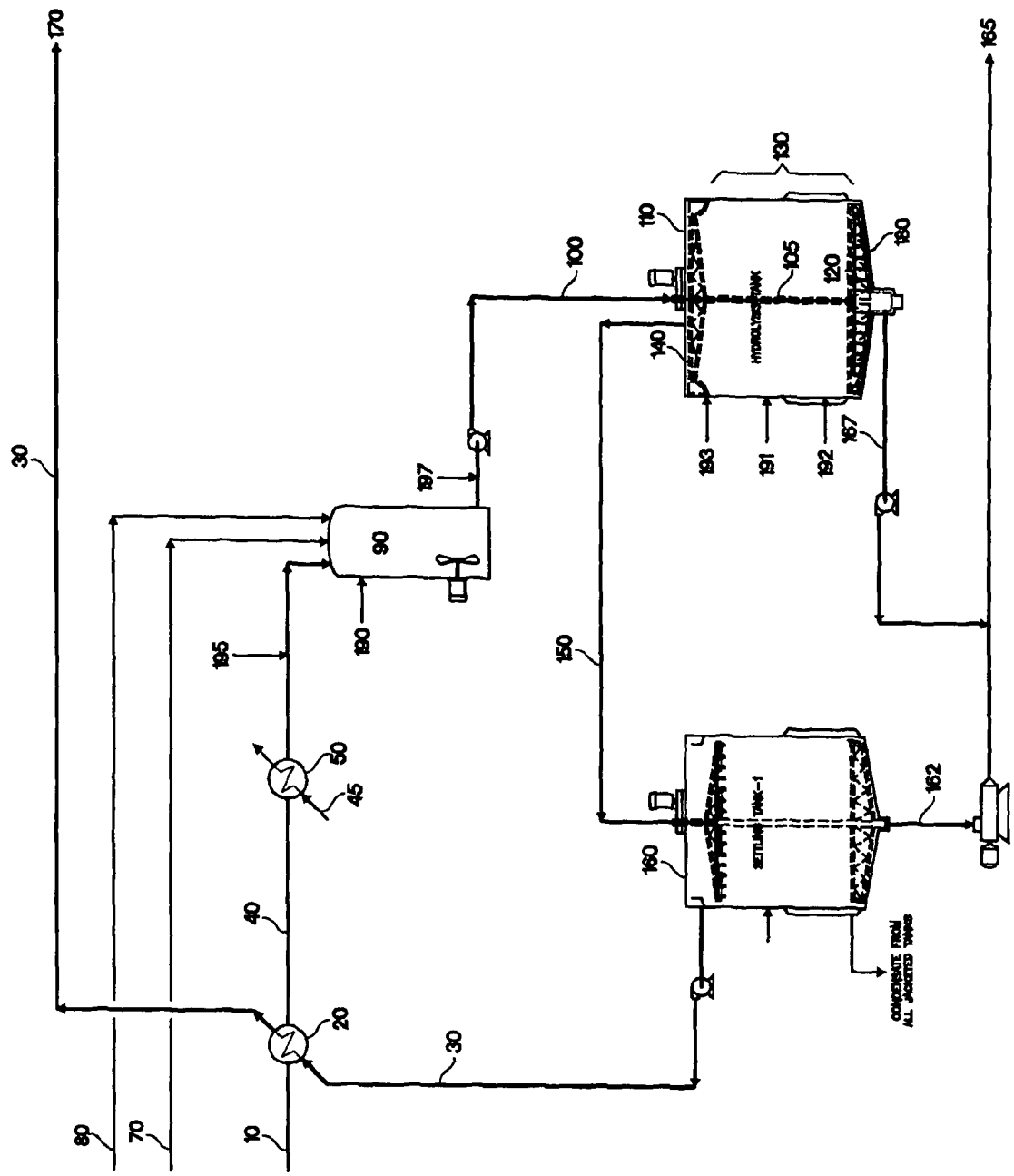
FIG. 1A shows the system comprising an upflow reactor and a settling tank.

The present invention relates to processes for the conversion of cellulosic feedstocks into products. More specifically, the present invention relates to processes having improved efficiency for enzymatic conversion of cellulosic feedstocks.

The following description is of a preferred embodiment by way of example only and without limitation to the combination of features necessary for carrying the invention into effect.

The invention relates to a process for the enzymatic conversion of cellulose to break down products, for example, but not limited to, glucose, cellobiose, glucose oligomers, or a combination thereof. In an aspect of the invention, the process involves pumping an aqueous cellulose slurry with cellulase upward in an unmixed hydrolysis reactor. The upward velocity of the slurry is slow, such that the solid particles, which are denser than the bulk slurry, tend to flow upward more slowly than the liquor. It is well established that cellulase enzymes bind tightly and preferentially to cellulose. The slow upward flow of the cellulose-containing solid particles retains the cellulose-containing solids and the bound cellulase enzyme in the reactor for a longer time than the liquid. The retention of cellulose and bound cellulase increases the conversion of cellulose to products, for example, glucose. Near the top of the reactor, the aqueous product or sugar stream and the unhydrolyzed solids are withdrawn. If the product is glucose, the aqueous sugar stream is withdrawn for fermentation to ethanol and other further processing. The process as described herein achieves a longer cellulose hydrolysis time within a smaller reactor than would otherwise be required for plug flow of the liquid and solids. Alternatively, the process as described herein achieves a higher cellulose conversion with less cellulase enzyme than would otherwise be required.

The present invention-provides a process for the enzymatic hydrolysis of cellulose to produce a hydrolysis product from a pre-treated cellulosic feedstock, the process comprising:

i) providing an aqueous slurry of the pre-treated cellulosic feedstock, the slurry comprising from about 3% to about 30% undissolved solids in a liquid, the undissolved solids comprising at least about 20% cellulose;

ii) introducing the aqueous slurry at the bottom of a hydrolysis reactor and limiting axial dispersion in the reactor by avoiding mixing, and maintaining an average slurry flow velocity of about 0.1 to about 20 feet per hour, such that the undissolved solids flow upward at a rate slower than that of the liquid;

iii) adding cellulase enzymes to the aqueous slurry before or during the step of introducing (step ii); and iv) removing an aqueous stream comprising hydrolysis product and unhydrolyzed solids from the hydrolysis reactor, the hydrolysis product comprising glucose, cellobiose, glucose oligomers, or a combination thereof.

Furthermore, in the step of adding (step iii), a flocculent may also be added to the slurry, either directly to the slurry, or along with the cellulase enzymes being added to the slurry.

The glucose may then be used for further processing to produce a product of interest, for example, but not limited to, ethanol.

Even though the upflow settling reactor, and process as described herein are suited to the enzymatic conversion of cellulose to glucose, this reactor and associated process may also be used to convert cellulose to other products, including, but not limited to, cellobiose (preferably if the enzyme, β-glucosidase (βG), is omitted from the cellulase) and glucose oligomers (preferably if the cellobiohydrolase enzymes (CBH) and βG are omitted from the cellulase). To further exemplify the present invention, the process for converting cellulose to glucose is described. However, it is to be understood that that this process may be used for the production of alternate products by incorporating different cellulase enzyme mixtures during hydrolysis of the feedstock.

By the term "cellulosic feedstock" or "cellulosic material", it is meant any type of biomass comprising cellulose such as, but not limited to, non-woody plant biomass, agricultural wastes and forestry residues and sugar-processing residues. For example, the cellulosic feedstock can include, but is not limited to, grasses, such as switch grass, cord grass, rye grass, miscanthus, or a combination thereof; sugar-processing residues such as, but not limited to, sugar cane bagasse and sugar beet pulp; agricultural wastes such as, but not limited to, soybean stover, corn stover, oat straw, rice straw, rice hulls, barley straw, corn cobs, wheat straw, canola straw, oat hulls, and corn fiber; and forestry wastes, such as, but not limited to, recycled wood pulp fiber, sawdust, hardwood, softwood, or any combination thereof. Further, the cellulosic feedstock may comprise cellulosic waste or forestry waste materials such as, but not limited to, newsprint, cardboard and the like. Cellulosic feedstock may comprise one species of fiber or, alternatively, cellulosic feedstock may comprise a mixture of fibers that originate from different cellulosic feedstocks. Wheat straw, barley straw, corn stover, soybean stover, canola straw, switch grass, reed canary grass, sugar cane bagasse, cord grass, oat hulls, sugar beet pulp and miscanthus are particularly advantageous as cellulosic feedstocks due to their widespread availability and low cost.

In principle, any material that contains a substantial amount of cellulose is suitable for the process of the present invention. In practice, the cellulosic material comprises cellulose in an amount greater than about 20% (w/w) to produce a significant amount of glucose. The cellulosic material can be of higher cellulose content, for example at least about 30% (w/w), 35% (w/w), 40% (w/w) or more. Therefore, the cellulosic material may comprise from about 20% to about 70% (w/w) cellulose, or from 25% to about 70% (w/w) cellulose, or about 35% to about 70% (w/w) cellulose, or more, or any amount therebetween, for example, but not limited to, 20, 22, 24, 25, 26, 28, 30, 32, 34, 35, 36, 38, 40, 42, 44, 46, 48, 50, 52, 54, 56, 58, 60, 62, 64, 66, 68 and 70% (w/w) cellulose.

The present invention may be practiced with a natural cellulosic feedstock or a cellulosic material that has been processed or pre-treated. Processing and pre-treatment methods are intended to deliver a sufficient combination of mechanical and chemical action so as to disrupt the fiber structure and increase the surface area of feedstock accessible to cellulase enzymes. Mechanical action typically includes, but is not limited to, the use of pressure, grinding, milling, agitation, shredding, compression/expansion, or other types of mechanical action. Chemical action can include, but is not limited to, the use of heat (often steam), acid, and solvents. Several chemical and mechanical pre-treatment methods are well known in the art.

One approach to pre-treatment of the feedstock is steam explosion, using the process conditions described in U.S. Pat. No. 4,461,648, and U.S. Pat. No. 4,237,226 (which are herein incorporated by reference). In this process, lignocellulosic biomass is loaded into a steam gun in the presence of 0% to 5% (v/v), or any amount therebetween, sulfuric acid or any other suitable acid. The steam gun is then filled rapidly with steam to a temperature of about 160° C. to about 280° C., or any amount therebetween, and held at high pressure for a cooking time of between about 3 seconds to about 30 minutes, or any amount therebetween. The vessel is then rapidly depressurized to expel the pre-treated biomass. Any parameters known in the prior art to effect steam explosion pre-treatments such as, but not limited to, those described in Foody, et al., (Final Report, Optimization of Steam Explosion Pre-treatment, U.S. Department of Energy Report ET230501, April 1980; which is herein incorporated by reference) may be used in the method of the present invention. The conditions chosen for steam explosion will depend upon the nature of the feedstock and the desired degree of susceptibility to enzymes. However, other methods that are known within the art may be used as required for preparation of a pre-treated feedstock, for example, but not limited to, those disclosed in U.S. Pat. No. 5,846,787 (Ladisch), U.S. Pat. No. 5,198,074 (Villavicencio), U.S. Pat. No. 4,857,145 (Villavicencio), or U.S. Pat. No. 4,556,430 (Converse; which are incorporated herein by reference), ammonia freeze explosion (U.S. Pat. No. 5,171,592, Holtzapple) and concentrated alkali treatment.

Regardless of whether a pre-treatment step is performed, the cellulosic feedstock may optionally be washed with water, or leached with water, for example, as disclosed in WO 02/070753 (Griffin et al., which is incorporated herein by reference) prior to enzymatic hydrolysis. Washing of pre-treated cellulosic feedstock can remove inhibitors of cellulase enzymes such as dissolved sugars and sugar degradation products, dissolved lignin and phenolic compounds, and other organic compounds in the system. The concentration of cellulose within washed pre-treated feedstock typically increases, for example up to levels of about 50%-70%.

The cellulosic material is slurried in a liquid at a concentration that is thick and can still be pumped. For example, but without wishing to be limiting, the liquid may be water, a recycled process stream or treated effluent. The concentration of cellulosic feedstock in the slurry depends on the material, but may be between about 3% to about 30% (w/w) undissolved solids, or any concentration therebetween, for example, from about 5% to about 20%, or from about 10% to about 20% undissolved solids, or any amount therebetween. For example, the concentration of cellulosic feedstock in the slurry may be 3, 5, 6, 8, 10, 12, 14, 16, 18, 20, 22, 24, 26, 28 or 30% undissolved solids (w/w). As is well known in the art, the concentration of suspended or undissolved solids can be determined by filtering a sample of the slurry using glass microfiber filter paper, washing the filter cake with water, and drying the cake overnight at 105° C.

The pH of the slurry is generally adjusted to within the range of optimum pH for the cellulase enzymes used. Generally, the pH of the slurry is adjusted to within the range of about 3.0 to about 7.0, or about 4.0 to about 6.0, or any pH therebetween, preferably within the range of about 4.5 to about 5.5. For example, the pH may be about 3.0, 3.5, 4.0, 4.5, 4.6, 4.7, 4.8, 4.9, 5.0, 5.1, 5.2, 5.3, 5.4, 5.5, 6.0, 6.5 or 7.0. The pH of the slurry may be adjusted using any suitable acid or base known in the art. For example, sodium hydroxide, ammonia, ammonium hydroxide, potassium hydroxide or other suitable base (if the slurry is acidic), or sulfuric acid, or other suitable acid (if the slurry is alkaline), may be used. However, the pH of the slurry can be higher or lower than about 4.5 to 5.5 if the cellulase enzymes used are alkalophilic or acidophilic, respectively. The pH of the slurry should be adjusted to within the range of optimum pH for the enzymes used.

The temperature of the slurry is adjusted to the point that is within the optimum range for the activity of the cellulase enzymes. Generally, a temperature of about 45° C. to about 70° C., or about 45° C. to about 65° C., or any temperature therebetween, is suitable for most cellulase enzymes. For example, the temperature of the slurry may be adjusted to about 45, 46, 47, 48, 49, 50, 51, 52, 53, 54, 55, 56, 57, 58, 59, 60, 61, 62, 63, 64, 65, 66, 67, 68, 69 or 70° C. However, the temperature of the slurry may be higher for thermophilic cellulase enzymes.

Cellulase enzymes are then added to the slurry. By the term "cellulase enzymes", "cellulase", or "enzymes", it is meant enzymes that catalyse the hydrolysis of cellulose to products such as glucose, cellobiose, and other cellooligosaccharides. Cellulase is a generic term denoting a multienzyme mixture comprising exo-cellobiohydrolases (CBH), endoglucanases (EG) and β-glucosidases (βG) that can be produced by a number of plants and microorganisms. The process of the present invention can be carried out with any type of cellulase enzymes, regardless of their source; however, microbial cellulases are generally available at lower cost than those of plants. Among the most widely studied, characterized, and commercially produced cellulases are those obtained from fungi of the genera *Aspergillus, Humicola*, and *Trichoderma*, and from the bacteria of the genera *Bacillus* and *Thermobifida*. Cellulase produced by the filamentous fungi *Trichoderma longibrachiatum* comprises at least two cellobiohydrolase enzymes termed CBHI and CBHII and at least 4 EG enzymes.

Cellulase enzymes work synergistically to degrade cellulose to glucose. CBHI and CBHII generally act on the ends of the glucose polymers in cellulose microfibrils liberating cellobiose (Teleman et al. 1995, European J. Biochem 231:250-258), while the endoglucanases act at random locations on the cellulose. Together these enzymes hydrolyse cellulose to smaller cello-oligosaccharides such as cellobiose. Cellobiose is hydrolysed to glucose by β-glucosidase.

The cellulase enzyme dosage added to the slurry is chosen to achieve a sufficiently high level of cellulose conversion without overdosing. For example, an appropriate cellulase dosage can be about 1.0 to about 40.0 FPU per gram of cellulose, or any amount therebetween. For example, the cellulase dosage may be about 1.0, 3.0, 5.0, 8.0, 10.0, 12.0, 15.0, 18.0, 20.0, 22.0, 25.0, 28.0, 30.0, 32.0, 35.0, 38.0 or 40.0 FPU per gram, or any amount therebetween. The FPU (Filter Paper Unit) is a standard measurement familiar to those skilled in the art and is defined and measured according to Ghose (1987, Pure and Appl. Chem. 59:257-268). For complete conversion to glucose, it is preferred that the cellulase contain an adequate quantity of β-glucosidase (cellobiase) activity. The dosage level of β-glucosidase is about 5 to about 600 β-glucosidase units per gram of cellulose, or any amount therebetween. A typical dosage level of β-glucosidase is about 10 to about 400 β-glucosidase units per gram of cellulose, or any amount therebetween; for example, the dosage may be 10, 12, 15, 17, 20, 22, 25, 27, 30, 32, 35, 37, 40, 42, 45, 47, 50, 52, 55, 57, 60, 62, 65, 67, 70, 72, 75, 77, 80, 82, 85, 87, 90, 92, 95, 97, 100, 120, 140, 160, 180, 200, 220, 240, 260, 280, 300, 320, 340, 360, 380 and 400 β-glucosidase units per gram of cellulose, or any amount therebetween. The β-glucosidase unit is measured according to the method of Ghose (1987, Pure and Appl. Chem. 59:257-268).

The cellulase enzymes may be handled in an aqueous solution, as a powder or as a granulate. The enzymes may be added to the slurry at any point prior to its entry into the reaction vessel (also referred to as a hydrolysis tower or hydrolysis reactor; 110 or 110', FIG. 1). For example, but without wishing to be limiting, the cellulase enzymes may be added to the slurry immediately prior to entering the hydrolysis tower. The enzymes may be mixed into the slurry using mixing equipment that is familiar to those of skill in the art. In a non-limiting example, a small make-up tank (90, FIG. 1A) located upstream of the main hydrolysis reactor (110 or 110') may be used for adding the enzymes to the slurry, adjusting the pH and achieving the desired temperature of the slurry.

With reference to FIG. 1A, the feedstock 10 is pre-treated as described above. This stream is cooled using a heat exchanger 20 that exchanges against product stream 30 or other suitable fluid. The slurry 40 may then be further cooled using a second fluid, for example cold water 45, at heat exchanger 50. The slurry may then be pumped into a hydrolysis make-up tank 90, along with cellulase enzymes 70 and ammonium hydroxide 80, to adjust the pH. In this example, the contents of the hydrolysis make-up tank 90 are mixed and pumped out of the make-up tank 90, along pipe 100, to the hydrolysis tank 110. However, the cellulase enzymes may be mixed with the feedstock elsewhere, for example, at 190, 195 or 197 or within a line that feeds the hydrolysis reactor, including, but not limited to, line 10, 40 or 100, or a combination thereof.

Figure 1B:
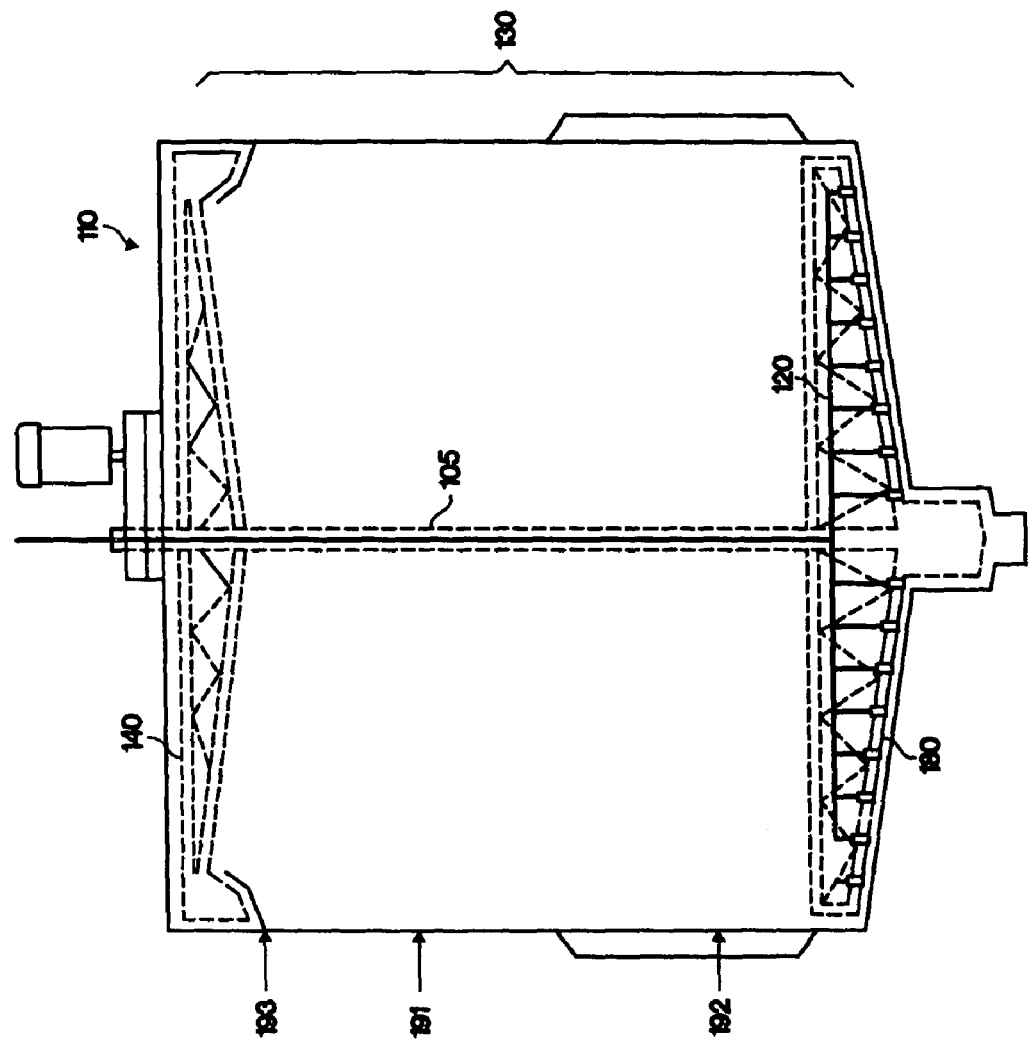
FIG. 1B shows the upflow reactor of FIG. 1A.
Figure 1C:
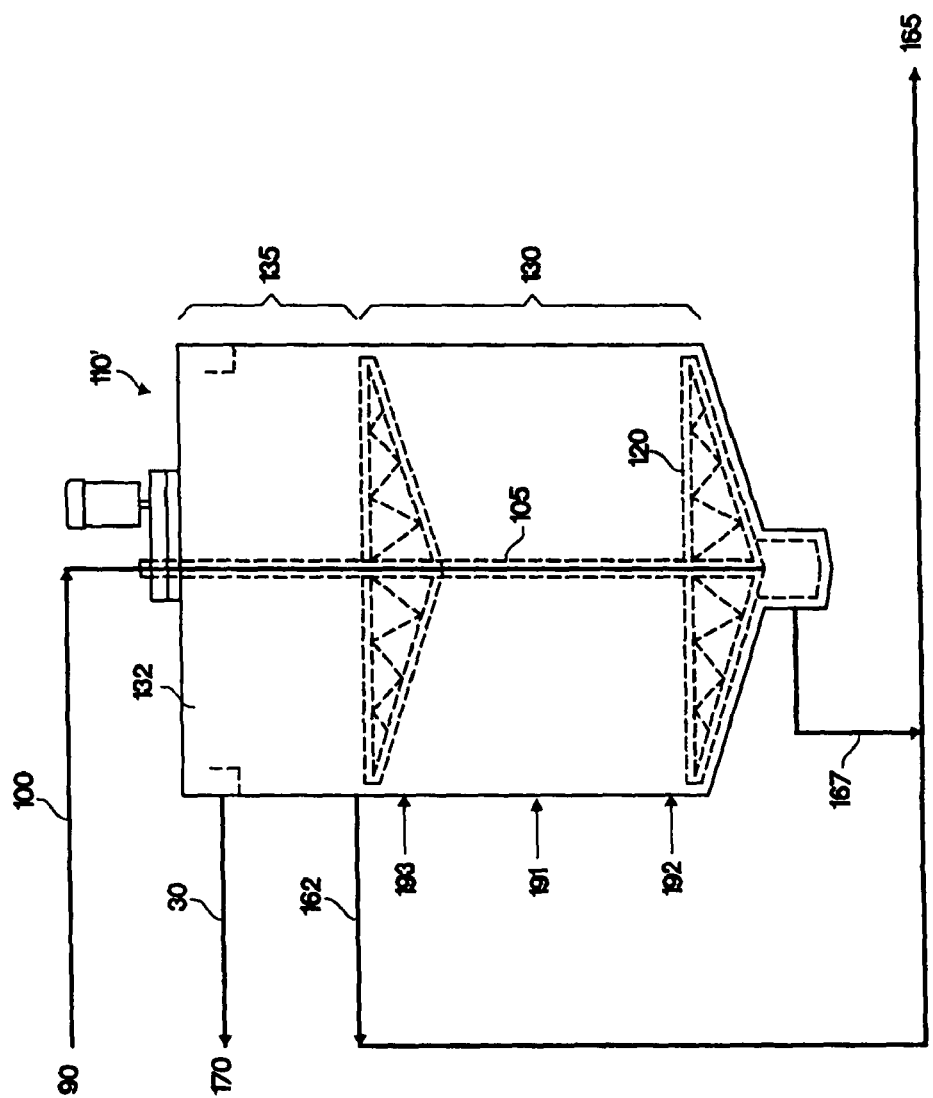
FIG. 1C shows a portion of the system where the upflow reactor comprises a clarifier zone.

By the term "hydrolysis tower", "upflow hydrolysis reactor", "hydrolysis reactor" "hydrolysis tank", or "upflow settling reactor", it is meant a reaction vessel (tower) of appropriate construction to accommodate the hydrolysis of cellulosic slurry by cellulase enzymes, for example 110 (FIG. 1B) or 110' (FIG. 1C). The hydrolysis tank may be jacketed with insulation, steam, hot water, electrical heat tracing, or other heat source to maintain the desired temperature. In the present application, the hydrolysis reactor is an unmixed hydrolysis reactor, in the sense that no mixing of the reactor contents takes place during the hydrolysis reaction. As set out below, some small amount of localized mixing of the reactor contents may occur due to the small amount of power input associated with the addition and withdrawal of solids and liquids from the system. The slurry and cellulase mixture may enter the upflow settling reactor directly at the bottom and be pumped upward in the hydrolysis tower; alternatively, the slurry can be pumped downward through a pipe located in the centre (e.g. 105) of the reactor and emerge at the bottom of the reactor to flow upward, surrounding the pipe. The latter configuration is advantageous in that heat from the slurry can be captured in the hydrolysis reactor. Once the slurry reaches the bottom of the hydrolysis tank 110 or 110', the slurry moves upward and is dispersed across the width of the hydrolysis tank; axial dispersion (i.e. dispersion along the height of the tank) is minimized by avoiding mixing. The slurry flow velocity is chosen such that the liquid component of the slurry flows upward at a rate faster than that of the undissolved solids. The hydrolysis tower is designed such that the contents of the slurry are relatively uniform in the radial direction, at any given height. The uniform distribution may be achieved using distributors (e.g. 120), or other equipment well known in the art. This may include fractal distributors (for example, Rohn Haas Advanced Amerpack™ system manufactured by Amalgamated Research Inc.) or a rotating wand. For example, in FIG. 1B, a vertical control shaft supports a pair of cantilevered truss arms at the bottom of the reactor 110 and another pair at the top of the reactor. The arms incorporate a header system with nozzles to distribute the product at the bottom of the vessel and to collect it at the top. A two-port rotary joint is used for the feed and the discharge from the central shaft. The distribution of the slurry within the hydrolysis tank is achieved in the absence of active mixing by impellers or pumps.

FIG. 1C shows an alternate hydrolysis tower 110' comprising a clarifier zone 135 positioned at the top of the tank. As described in more detail below, the majority of the solids are withdrawn at the top of zone 130. Excess clarified liquid continues to flow upward in zone 135 and is withdrawn as clear liquid.

The hydrolysis reactor 110 or 110' may be of any dimensions that will maintain a relatively uniform slurry concentration across the reactor, as described. Without wishing to be limiting, the hydrolysis tower may have a diameter of between about 10 feet to about 130 feet (3 to 40 m), or any amount therebetween; for example, the diameter of the reactor may be 10, 15, 20, 25, 30, 35, 40, 45, 50, 55, 60, 65, 70, 75, 80, 85, 90, 95, 100, 105, 110, 115, 120, 125, or 130 feet, or any amount therebetween. The height of the hydrolysis reactor can be of any height, provided that the reactor achieves the purposes herein described. Without wishing to be limiting, the reactor height may be of about 5 to about 75 feet or about 5 to about 65 feet (1.5 to 23 m), or any amount therebetween, preferably from about 20 to about 65 feet; for example, the reactor height may be about 5, 7.5, 10, 12.5, 15, 17.5, 20, 22.5, 25, 27.5, 30, 32.5, 35, 37.5, 40, 42.5, 45, 47.5, 50, 52.5, 55, 57.5, 60, 62.5, or 65 feet. The height-to-diameter ratio of the hydrolysis reactor may be between about 0.5 to about 10, or any ratio therebetween; preferably the height-to-diameter ratio is from about 0.5 to about 3. The overall size of the reactor should be chosen so as to avoid placing an undue burden on the foundation supporting the reactor when it is filled with water. In a non-limiting example, a hydrolysis reactor having a diameter of 110 feet and height of 65 feet would have a volume of 4.60 million gallons.

The slurry is pumped upward into the reactor 110 or 110' at an average slurry flow velocity that allows the liquid to flow uniformly up the reactor while the cellulose-containing particles, which are denser than the liquid, flow up the reactor more slowly than the liquid, settle, and pack to some solids concentration that is higher than the feed solids concentration. The "average flow velocity" of the slurry or "slurry flow velocity" is the height of the hydrolysis reactor divided by the nominal slurry residence time, based on the reactor volume and the slurry flow rate to the reactor. For example, a slurry feed rate of 10,000 gallons per hour to a 120,000 gallon hydrolysis reactor that is 30 feet tall has a nominal slurry residence time of 120,000 gallons/(10,000 gallons/hr)=12 hours and an average slurry flow velocity of 30 ft/12 hr=2.5 ft/hr. The average flow velocity is selected to permit solids to flow upward at a slower rate than the average slurry flow velocity. This permits the solids to have a longer average residence time in the hydrolysis reactor than the nominal slurry residence time. This differs from slurry plug flow reactors in which the flow velocity and the retention time of the liquid and solids in the reactor are substantially the same. The flow velocity at which this is achieved will be dependent on the feedstock and the size of the solid particles in the slurry, as well as the presence of any added flocculent. The use of a flocculent may permit the use of a higher average flow velocity. Generally, the average flow velocity is about 0.1 to about 20 feet per hour, or any velocity therebetween. Preferably, the average flow velocity is between about 0.1 to about 12 feet per hour, or any amount therebetween. More preferably, the average flow velocity is between about 0.1 to about 4.0 feet per hour, or any amount therebetween. For example, the average slurry flow velocity may be about 0.1, 0.2, 0.3, 0.4, 0.5, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0 12.5, 13.0, 13.5, 14.0, 14.5, 15.0, 15.5, 16.0, 16.5, 17.0, 17.5, 18.0, 18.5, 19.0, 19.5, or 20.0 feet per hour. The nominal slurry residence time in the hydrolysis reactor is typically 4-120 hours, preferably 12-100 hours and most preferably 20-100 hours.

Using the method of the present invention, the properties of the slurry will change as hydrolysis of cellulose proceeds. Without wishing to be bound by theory, during the hydrolysis reaction, the cellulase enzymes bind to the cellulose and therefore remain bound to the cellulose-containing solid particles in the slurry. The average upward velocity of the slurry is slow, such that the solid particles, which are denser than the bulk slurry, tend to flow upward more slowly than the liquor. The slow upward flow of the cellulose-containing solid particles retains the cellulose-containing solids and the bound cellulase enzyme in the reactor for a longer time than the liquid. As the bound enzymes digest the cellulose and release glucose into solution, the amount of cellulose, and the density of the solid particles, changes. Depending on the altered density, smaller particles will flow upward with the liquid or settle to the bottom of the reactor. Due to the differential retention of the cellulose-containing particles relative to the liquor, the concentration of cellulose will decrease from the bottom to the top of the hydrolysis reactor while the concentration of glucose will increase from the bottom to the top of reactor. The decrease in the concentration of cellulose, and an increase in the concentration of glucose, occurs in the "hydrolysis zone" 130 of the hydrolysis reactor 110 (see FIGS. 1A and 1B). The aqueous sugar stream, the unhydrolyzed solids, and any nearby cellulose-containing particles are withdrawn 150 near the top of the hydrolysis zone 140 of the reactor 110. At least a portion of the solids are then separated from the glucose stream, for example using a solids-liquid separator, for example, settling tank 160 and the product stream 30 is sent for fermentation to ethanol and other further processing (170). The longer retention of cellulose within the hydrolysis tower increases the extent of conversion of the cellulose to glucose, thereby achieving a longer cellulose hydrolysis time with a smaller reactor than would be achieved with a mixed reactor. Alternatively, a higher cellulose conversion is achieved with a lower enzyme dosage than would be required otherwise.

By the term "unhydrolyzed solids" or "unconverted solids", it is meant cellulose that is not digested by the cellulase enzyme, as well as non-cellulosic, or other, materials that are inert to cellulase, present in the feedstock. For example, but without wishing to be limiting in any manner, the unconverted solids may comprise lignin, silica or other solid material. As the cellulose in the feedstock is hydrolyzed, the concentration of unconverted solids within the cellulose-containing solid particles increases. Depending on the density and particle size, the unconverted solids may be removed with the products at 150 or settle to the bottom in a sediment or sludge 180. If a sludge layer forms at the bottom of the reactor due to very heavy particles, any means known in the art may be employed to remove the sludge or sediment. In a non-limiting example, a scraper may be used to remove the sludge. In a further example, the bottom of the reactor may be tapered to provide a path in which the heaviest solids may settle, and be removed (e.g. line 167) and sent for lignin processing 165.

The aqueous glucose, unconverted solids and other particles that are found near the top 140 of the hydrolysis reactor 110 can be removed as a stream 150. Following withdrawal from the top of the reactor, at least a portion of the unconverted solids may be separated from the soluble sugar stream. Removal of the unconverted solids can be accomplished using a solids-liquid separator, for example by filtration (for example, a filter press, belt filter, drum filter, vacuum filter or membrane filter), centrifugation, settling, for example, settling tank 160, an inclined settler (for example, as disclosed in Knutsen and Davis, 2002, Appl., Biochem. Biotech., 98-100: 1161-1172 and Mores et al., 2001, Appl. Biochem. Biotech., 91-93:297-309, both of which are incorporated herein by reference), a clarifier, or any other suitable process as would be known in the art. The clarifier may comprise a number of inclined plates to facilitate the separation of the solids and liquid or other features that are known in the art of solids-liquid separation. The soluble glucose, essentially free of undissolved solids, is then suitable for fermentation to ethanol (170). The unconverted solids are primarily lignin, which can be burned and used as fuel for the plant.

Alternatively, the aqueous glucose stream is withdrawn at a location separate from the withdrawal of unconverted solids. An alternative method for separating the unconverted solids from the glucose is to use the reactor 110' in FIG. 1C with a hydrolysis zone 130 extending from the bottom of the hydrolysis tower to a level about 65% to about 85% of the way up, and a "clarifier zone" 135 directly above the hydrolysis zone. The hydrolysis stream is pumped from the top portion of the hydrolysis zone 130 into the clarifier zone 135. A majority of the solids are removed at the top of the hydrolysis zone 130. For example, but not wishing to be limiting in any manner, a horizontal wand with nozzles is passed back and forth across the top of the reactor at time intervals, and the solids-rich stream is withdrawn into the wand and pumped out of the reactor (162). Excess clarified liquid continues to flow upward into clarifier zone 135. In the clarifier zone 135, the solids generally settle to the level of the wand, while the aqueous sugar stream, essentially free of solids, is removed (30) from the top. The clarifier zone may comprise a number of inclined plates to facilitate the separation of the solids and liquid and other features that are known in the art of solids-liquid separation. The unconverted solids (or unhydrolyzed solids) may be transferred to a solids-liquid separator to separate at least a portion of the hydrolysis product from the unhydrolyzed solids.

If so desired, the cellulose-containing solids obtained by separation from the glucose stream can be recycled back into the upflow settling reactor, or the hydrolysis zone, with the incoming feedstock for further conversion to glucose.

It should be appreciated that some small amount of localized mixing of the reactor contents may occur due to the small amount of power input associated with the addition and withdrawal of solids and liquids from the system. For example, localized mixing may occur due to the action of the distributors 120, wands or pump(s) that feed the slurry into the hydrolysis reactor. For best operation, the power required for carrying out addition and withdrawal of solids and liquids associated with the operation of the hydrolysis reactor does not exceed 0.1 HP/1000 gal. The power associated with these upflow reactor functions may be between 0.001 and 0.1 HP/1000 gal, or any range therebetween. For example, the power associated with these upflow reactor functions may be 0.001, 0.003, 0.008, 0.01, 0.02, 0.03, 0.04, 0.05, 0.06, 0.07, 0.08, 0.09 or 0.1 HP/1000 gal. There are no impellers, agitators, eductors, or other equipment in the reactor specifically designed to mix the slurry.

If more than one hydrolysis reactor is employed, the reactors may be run in a series of two or more than two reactors, in which case the outlet of a first reactor feeds the inlet of a second reactor. Alternatively, the reactors may be run in parallel. Furthermore, some of the reactors in the sequence may be run in series, while others may be run in parallel.

It should also be appreciated that one or more other reactor types in addition to the upflow reactor may be utilized, such as one or more batch or continuous stirred reactors. In a non-limiting example, the outlet of a continuous stirred reactor feeds the inlet of an upflow reactor. As would be apparent to one of skill in the art, other combinations of reactor types may be used in the present invention.

In an alternative aspect of the present invention, flocculating compounds may be added to the slurry to enhance the efficiency of the present invention. Flocculating compounds are typically polymers that are cationic, nonionic, anionic, or amphoteric (containing a mixture of charged groups), or salts such as alum. Without wishing to be bound by theory, flocculating compounds serve to aggregate the solids within the hydrolysis reactor to ensure a more complete exposure to the enzyme mixture.

In practising the present invention, one flocculating compound, or a mixture containing more than one flocculating compound, may be used. The flocculent may be provided in any suitable form for addition to the slurry; for example, the flocculent may be a powder, a liquid, or a dispersion; for example, the dispersion may be a flocculent slurried in oil or an aqueous solution. A non-limiting example of a suitable flocculent is a cationic polymer, more specifically, a polyacrylamide. Such flocculants include, but are not limited to, CA4500 (SNF Floerger®, France) and Zetag® 7651 (Ciba® Specialty Chemicals, Canada).

The amount of flocculent used will be determined by the amount necessary to aggregate the solids in the upflow reactor. A person of skill in the art will be able to determine the amount of flocculent to add that would aid in solids-aggregation, without the addition of undesirable cost to the overall process. For example, but without wishing to be limiting, the amount of flocculent added may be an amount in the range of about 0.1 to about 4.0 kg per tonne solids or any amount therebetween, or about 0.5 to about 2.0 kg per tonne solids, or any amount therebetween. For example, the amount of flocculent added may be about 0.1, 0.5, 0.75, 1.0, 1.25, 1.5, 1.75, 2.0, 2.5, 3.0, 3.5, or 4.0 kg per tonne solids.

Flocculating compounds may be added directly to the slurry, or dispersed and diluted in water prior to addition to the slurry. The flocculating compounds can also be mixed with the cellulase enzymes before addition to the slurry. Dispersion of the flocculent may help ensure uniform application of the flocculent in the system. In a non-limiting example of the present invention, the flocculent may be dispersed in water at a concentration of about 0.01% to about 25% by weight, or any amount therebetween; for example, the concentration of flocculent may be about 0.01, 0.02, 0.04, 0.06, 0.08, 0.1, 0.15, 0.2, 0.25, 0.3, 0.35, 0.4, 0.45, 0.5, 1.0, 2.0, 3.0, 4.0, 5.0, 7.0, 10.0, 12.0, 14.0, 16.0, 18.0, 20.0, 22.0, or 25.0% by weight. The flocculent may be dispersed at this concentration by mixing for an appropriate amount of time, for example about 1 minute to about 1 hour. The dispersed flocculent may then be added directly to the cellulose slurry, or be further diluted in water to a concentration of about 0.01% to about 1.0%, by weight, or any amount therebetween, prior to addition to the hydrolysis reactor. For example, the concentration of the further diluted flocculent may be 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, or 1.0% by weight.

The present invention therefore provides a system for hydrolyzing cellulose to glucose, cellobiose, glucose oligomers, or a combination thereof, the system comprising a feedstock slurry supply line (e.g. 10, 40, 100) in fluid communication with an input to an upflow hydrolysis reactor (e.g. 110 or 110'), a solids-liquid separator (e.g. 160 or 135) in fluid communication with the upflow hydrolysis reactor and comprising a first output for withdrawing a slurry comprising unhydrolyzed solids and a second output for withdrawing a stream comprising hydrolysis product, the hydrolysis product comprising glucose, cellobiose, glucose oligomers, or a combination thereof, wherein the feedstock supply line, the upflow hydrolysis reactor, or both the feedstock supply line and the upflow hydrolysis reactor, comprise an enzyme composition comprising cellulase enzymes and one or more than one flocculent. Preferably, the feedstock supply line comprises a pre-treated feedstock prepared as outlined above. Furthermore, the cellulase enzymes within the system are present at a dosage from about 1.0 to about 40.0 FPU per gram of cellulose of the pre-treated feedstock, and the one or more than one flocculating compound is present at a dosage from about 0.1 to about 4.0 kg per tonne solids of the pre-treated feedstock.

The present invention also pertains to a use of an enzyme composition comprising cellulase enzymes and one or more than one flocculent, for hydrolyzing cellulose to glucose, cellobiose, glucose oligomers, or a combination thereof, as described herein. As this system results in about 60 to about 98% conversion of the cellulose to glucose, the glucose may be used for the production of ethanol. Preferably, the cellulase enzymes are produced by *Aspergillus, Humicola, Trichoderma, Bacillus, Thermobifida*, or a combination thereof. The one or more than one flocculating compound may be selected from the group consisting of a cationic polymer, a non-ionic polymer, an anionic polymer, an amphoteric polymer, salts, alum, and a combination thereof. Preferably, the one or more than one flocculating compound is the cationic polymer, for example a polyacrylamide. The cellulase enzymes and one or more than one flocculent as described herein may also be used for the preparation of an enzyme composition for hydrolyzing cellulose to glucose, cellobiose, glucose oligomers, or a combination thereof. Therefore, the present invention also provides a use of an enzyme composition comprising cellulase enzymes, and one or more than one flocculent, for hydrolyzing cellulose to glucose, cellobiose, glucose oligomers, or a combination thereof, for the production of ethanol.

The flocculent, or the diluted flocculent may be added prior to the point of enzyme addition (195; FIG. 1A) to the slurry, at the point of enzyme addition (190), after the point of enzyme addition (197), or a combination of these locations. Furthermore, the flocculent may be added to the slurry at or near the bottom of the hydrolysis reactor (192; FIGS. 1A, 1B and 1C), in the midsection of the hydrolysis reactor (191), at the top of the reactor (193), at a location outside the reactor (195, 197), or a combination of these locations. In a non-limiting example, flocculent may be added at the bottom (192) and in the midsection (191) of the reactor. If the flocculent inhibits or negatively impacts on enzyme activity, then the flocculent should not be in direct contact with the enzyme in a manner that might be deleterious to the enzyme prior to addition to the slurry or hydrolysis tank.

The flocculent may be added by pumping through a series of valves and elbows. Such a configuration may improve mixing of the flocculent with the slurry and prevent backing up of the mixture into the system. In an alternate example, an in-line mixer can be used to impart turbulence to the flocculent and thereby enhance the dispersion. Alternatively, the flocculent may be added to the slurry (e.g. at 190) in the make-up tank 90, then pumped to the hydrolysis reactor 110 or 110' along with the slurry and cellulase enzymes 40.

Once in the hydrolysis reactor 110 or 110', the flocculent proceeds to bind to the solid particles and aid in the aggregation in the hydrolysis zone 130. Without wishing to be bound by theory, this helps prevent the cellulose-containing particles from being removed out the top of the reactor, from settling in the sludge layer by keeping them suspended in the reactor, or a combination thereof. Binding the solid particles allows greater residence time for the cellulose-containing particles within the hydrolysis zone (130) and results in a more complete and efficient digestion of cellulose by the enzymes. At the top of the upflow reactor 140 the flocculent is primarily bound to the unconverted solids, and exits the reactor (150; FIG. 1A) with the particles.

It is contemplated that glucose produced by the hydrolysis of cellulose from the pre-treated feedstock that leaves the reactor 110 or 110' through line 30 may be fermented to ethanol (170). Fermentation of glucose and other sugars to ethanol may be performed by conventional processes known to those skilled in the art, and may be effected by a variety of microorganisms including yeast and bacteria or genetically modified microorganisms, for example, but not limited those described in WO 95/13362, WO 97/42307, or Alcohol production from Cellulosic Biomass: The Iogen Process (in: The Alcohol Textbook, Nottingham University Press, 2000; which are herein incorporated by reference). Ethanol production and recovery are performed using well-established processes known to one of skill in the art in the alcohol industry.

As indicated previously, the upflow settling reactor is suited to the enzymatic conversion of cellulose to glucose. However, this type of system can be used to convert cellulose to other products, including cellobiose (preferably if βG is omitted from the cellulase) and glucose oligomers (preferably if CBH and βG are omitted from the cellulase).

The method of the present invention increases the length of time that the solids are in the reactor, which increases the contact time between the cellulase enzymes and cellulose because the enzymes remain bound to the cellulose. This in turn increases the efficiency of the hydrolysis process by increasing the degree of cellulose conversion obtained in a hydrolysis reactor of a given size. Thus, the costs of enzymatic hydrolysis are minimized. Furthermore, the upflow settling method does not require agitation within the reactor, saving the power and equipment costs associated with mixing.

The above description is not intended to limit the claimed invention in any manner. Furthermore, the discussed combination of features might not be absolutely necessary for the inventive solution. The present invention will be further illustrated in the following examples. However, it is to be understood that these examples are for illustrative purpose only, and should not be used to limit the scope of the present invention in any manner.

EXAMPLES

Example 1

Large Scale Upflow Hydrolysis Reactor

Pre-treated wheat straw is prepared using the method of U.S. Pat. No. 4,461,648 (Foody, which is incorporated herein by reference). The pre-treated material is an aqueous slurry of 7.8% undissolved solids, at a temperature of 70° C., and a mass flow rate of 553 t/hr. This aqueous slurry is cooled to 60° C. in a heat exchanger (20), against the product stream (30). The 60° C. slurry is then cooled to a final temperature of 50° C. by cold water at heat exchanger (45). The slurry is pumped into the hydrolysis make-up tank (90; volume 86,000 gallons) along with cellulase enzymes (70; 5 FPU/g cellulose) and ammonia (80; 1200 grams per tonne wet slurry), to adjust the pH to 4.5 to 5.0. The contents of the hydrolysis make-up tank are mixed for a residence time of 40 minutes and then the combined stream (100) is pumped out of the make-up tank and down a pipe through the middle (105) of the hydrolysis tank (110). The hydrolysis tank is jacketed with 15 psig steam used to maintain 50° C. At the bottom of the hydrolysis tank, the slurry is pumped upward and dispersed (120) across the width of the hydrolysis tank.

The hydrolysis tank has a volume of 4.6 million gallons. The liquid flows upward in the hydrolysis tank faster than the solids, which settle to a concentration of about 10% throughout the tank. The cellulose is held up in the tank 188 hrs, which is long enough to convert 92% of the cellulose to glucose. The aqueous sugar stream and the unhydrolyzed solids (150) flow out of the top of the tank and are pumped to the settling tank (160). In the settling tank, which had a volume of 1.12 million gallons, the solids settle to the bottom to a concentration of 10% and are pumped out via line 162 to a lignin filter press 165 to recover sugar from the solids by pressing and washing. The sugar from this stream is combined with the sugar stream from the top of the settler, which is then sent for fermentation to ethanol (170).

Example 2

Upflow Hydrolysis with *Trichoderma* Cellulase Enzyme

Wheat straw was pre-treated using the method of U.S. Pat. No. 4,461,648 (Foody, which is incorporated herein by reference). The pre-treated material was slurried in water at a concentration of 3.7% undissolved solids and the pH was adjusted to 5.5 with 30% sodium hydroxide. The undissolved solids were 55% cellulose. The slurry was pumped at a rate of 40 liters per minute into the bottom of a vertical hydrolysis reactor (110; FIG. 1C). This corresponds to an upward flow velocity of 0.7 feet/hr. The tower volume was 144,700 liters, of which the hydrolysis zone (130) was the lower 115,000 liters (a height of 34.4 feet) and the top 29,700 liters was a clarifier (135). The diameter of the tower was 3.8 meters and the height was 13.5 meters (44.3 feet). The temperature of the slurry was 55° C. upon entry in the reactor, and gradually decreased to 50° C. near the top of the reactor. The cellulase enzyme, obtained from *Trichoderma* (available from Iogen Bioproducts, Ottawa) was added to the slurry in the hydrolysis make up tank (90; FIG. 1A) at a dosage of 36 FPU per gram cellulose, added to the line before entering the tower as in Example 1.

The slurry containing pre-treated solids and cellulase was pumped into the bottom of the tower 105 and hydrolysis took place as the slurry flowed up the tower. At the top of the hydrolysis zone, which was 79% of the volume of the tower, the slurry was transferred to a clarifier zone 135. A stream containing settled solids was withdrawn (162; FIG. 1C) at the interface of the hydrolysis zone and the clarifier zone. A second stream 30 containing glucose in the aqueous phase with little undissolved solids was collected at the top of the clarifier zone.

Figure 2:
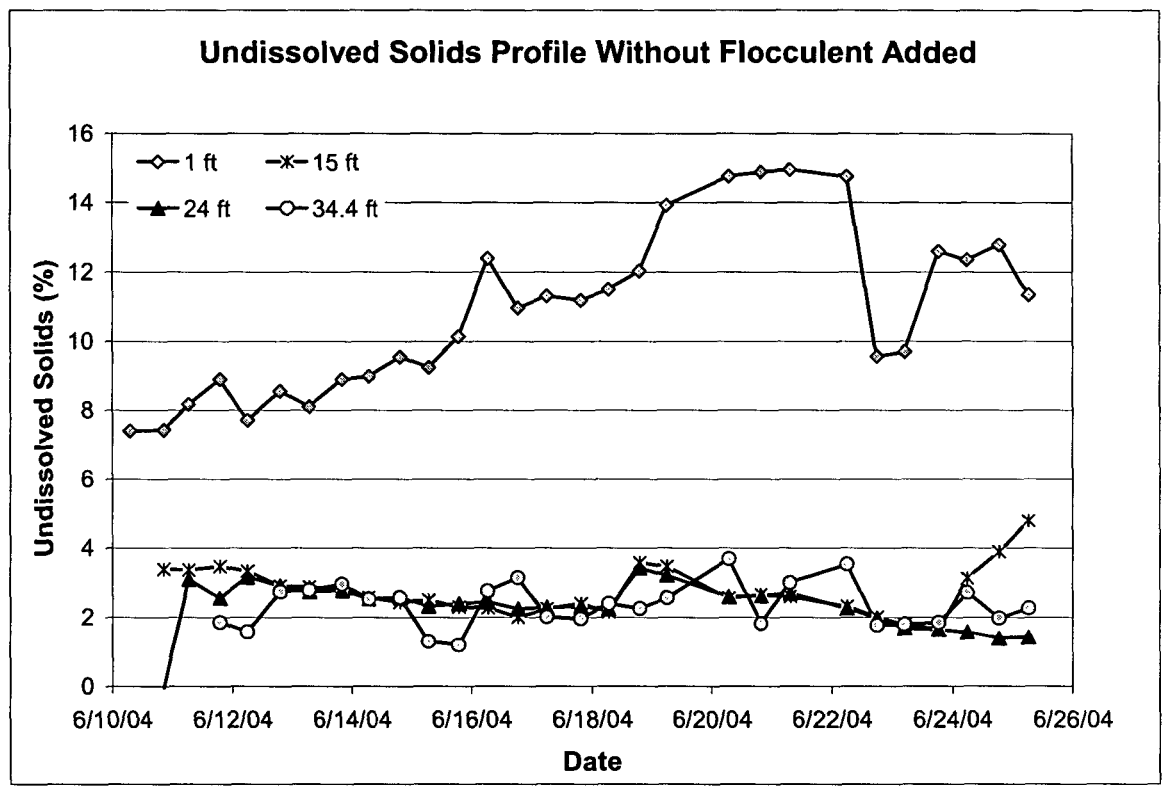
FIG. 2 shows the undissolved solids content sampled at various heights within the hydrolysis reactor in the absence of adding a flocculent.

The solids profile in the reactor over the course of the run is shown in FIG. 2. At a level of 1 foot above the bottom, the undissolved solids settled to a concentration of 8% to 14%, by weight. This was significantly more concentrated than the feed concentration of 3.7% undissolved solids. At points higher than this, the solids concentration was lower.

Figure 3:
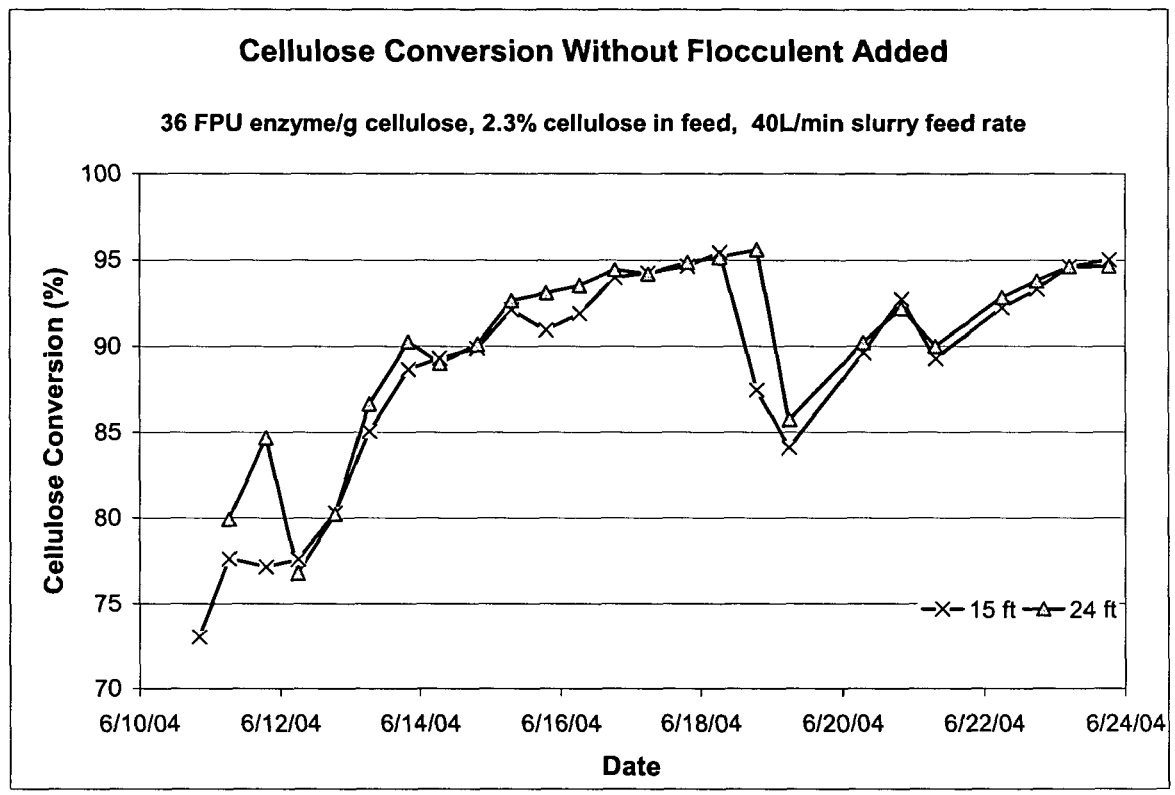
FIG. 3 shows the percentage of cellulose conversion measured by sampling at various heights within the hydrolysis reactor in the absence of adding a flocculent.

The cellulose conversion profile is shown in FIG. 3. The degree of cellulose conversion was 73% to 83% early in the run, and by the end was 95% at the heights of 15 feet and 24 feet. The glucose concentration in the stream flowing out of the upflow reactor was 25 g/L. This represents a good level of cellulose conversion and glucose production obtained without mixing a reactor, providing shear, or otherwise moving the material beyond pumping it slowly up the tower.

Example 3

Upflow Hydrolysis with *Trichoderma* Cellulase Enzyme in Presence of Flocculating Compound A hydrolysis of pre-treated wheat straw was carried out as described in Example 2 with 4.4% undissolved solids, except that a flocculent was added to improve the settling of the solids. A cationic polymer, CA4500 (SNF Floerger®, France), was added at a dosage of 2 kg per tonne undissolved solids and dispersed inline upon addition after the point of enzyme addition to the slurry.

Figure 4:
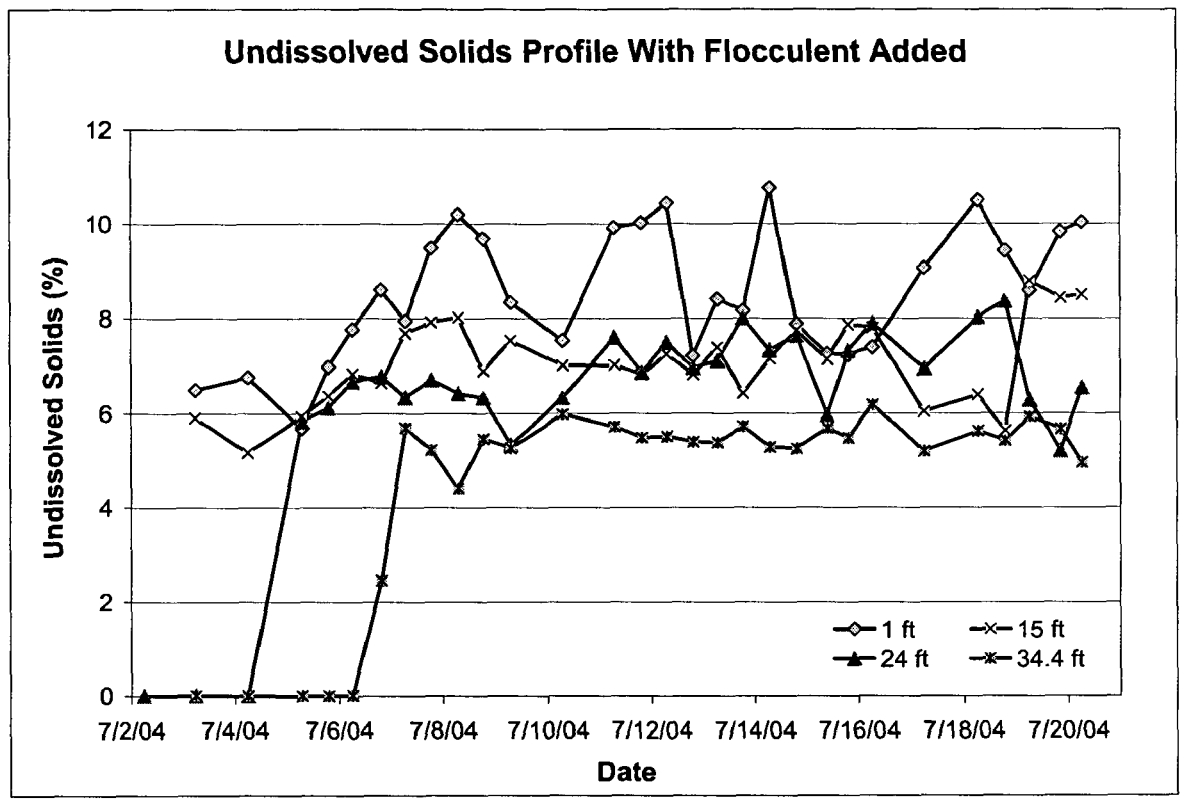
FIG. 4 shows the undissolved solids content sampled at various heights within the hydrolysis reactor in the presence of a flocculent.

The solids profile in the reactor over the course of the run is shown in FIG. 4. At a level of 1 foot above the bottom, the undissolved solids settled to a concentration of 6% to 10%, by weight, similar to that observed in Example 2, and was significantly more concentrated than the feed concentration of 4.4% undissolved solids. At points higher than this within the reactor, the solids concentration was 5.5% to 8%. This indicated the flocculent was effective at aggregating and settling the solids.

Figure 5:
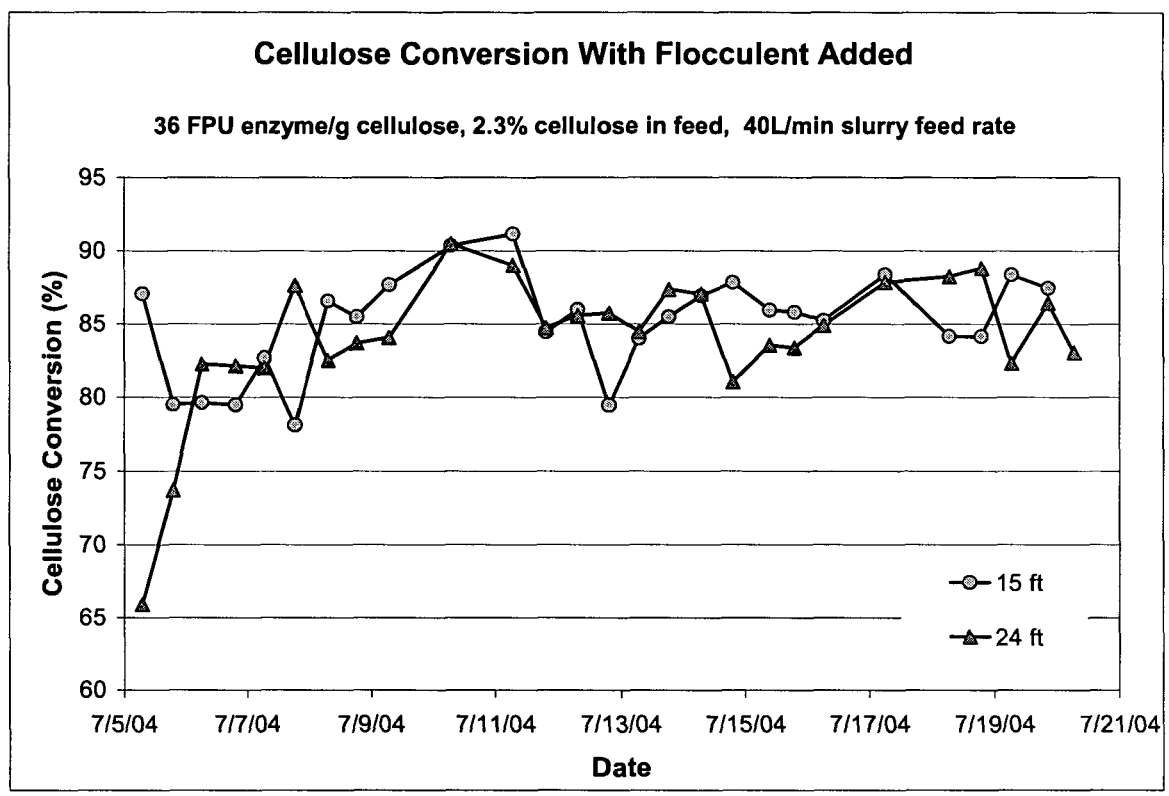
FIG. 5 shows the amount of converted cellulose sampled at various heights within the hydrolysis reactor in the presence of adding a flocculent.

The cellulose conversion profile is shown in FIG. 5. The degree of cellulose conversion was 65% to 85% early in the run, and by the end was 85% to 92% at the heights of 15 feet and 24 feet. The glucose concentration in the stream flowing out of the reactor was 27 g/L. This represents a good level of cellulose conversion obtained without mixing a reactor, providing shear, or otherwise moving the material beyond pumping it slowly up the tower.

Example 4

Cellulose Conversion at Various Enzyme Levels in Presence and Absence of Flocculating Compound The hydrolysis reactions described in Examples 2 and 3 showed a similar final glucose concentration, which may be due to the presence of an excess of enzymes. In order to determine the effect of flocculent on hydrolysis efficiency, hydrolysis was performed in the presence and absence of flocculent at various enzyme dosages.

A hydrolysis of pre-treated wheat straw is carried out as described in Examples 2 and 3, except that the amount of cellulase enzyme added is varied. A hydrolysis with 8, 12, 16, 20, 24, 28, 32, and 36 FPU enzyme is carried out in the presence and absence of flocculent for 48 hours. The cellulose conversion (in %) is measured and shown in FIG. 6.

Figure 6:
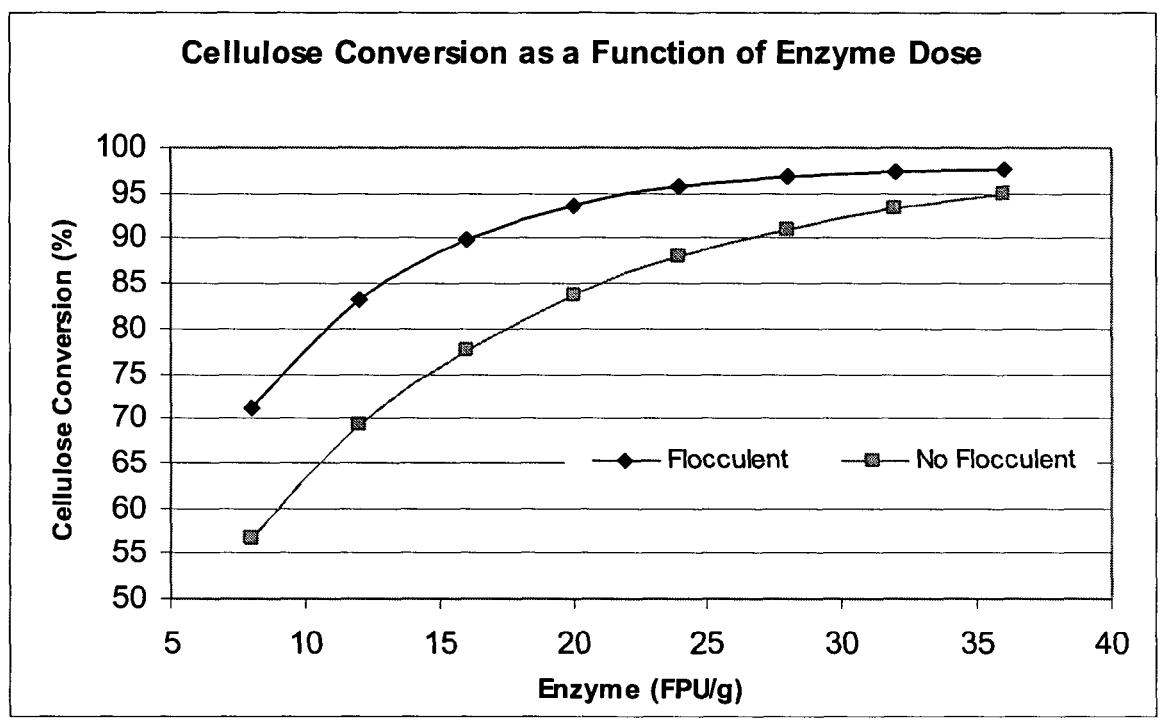
FIG. 6 shows an increase in efficiency in cellulose conversion in the product leaving the hydrolysis reactor in the presence of added flocculent compared to the absence of flocculent.

As shown in FIG. 6, at lower enzyme dosages, the use of flocculent results in increased cellulose conversion. This represents an overall saving in the cost of cellulose conversion.

The embodiments of the invention in which an exclusive property or privilege is claimed are defined as follows:

1. A process for the enzymatic hydrolysis of cellulose to produce glucose from a pre-treated cellulosic feedstock, the process comprising:

i) providing an aqueous slurry of the pre-treated cellulosic feedstock, the slurry comprising from about 3% to about 30% undissolved solids in a liquid, the undissolved solids comprising at least about 20% cellulose;

ii) introducing the aqueous slurry at the bottom of an unmixed hydrolysis reactor having a height of between about 5 and about 75 feet and a height-to-diameter ratio of between about 0.5 and about 10 and limiting axial dispersion in the unmixed hydrolysis reactor by pumping the slurry upwardly at a velocity that corresponds to an average slurry flow velocity in said unmixed hydrolysis reactor of about 0.1 to about 12 feet per hour, and wherein the undissolved solids flow upward at a rate slower than that of the liquid;

iii) adding cellulase enzymes and β-glucosidase to the aqueous slurry before or during the step of introducing (step ii), or a combination thereof, wherein the cellulase enzymes hydrolyze the cellulose to produce the glucose and wherein the glucose so produced has a higher concentration at the top of the unmixed hydrolysis reactor than at its bottom; and iv) removing an aqueous upflowing stream comprising at least the glucose from the unmixed hydrolysis reactor.

2. The process according to claim 1, wherein, in the step of introducing (step ii), the aqueous slurry is introduced at the bottom of the hydrolysis reactor with a uniform radial distribution.

3. The process according to claim 1, wherein, in the step of adding (step iii), one or more than one flocculating compound is added to the aqueous slurry, separately from, or together with the cellulase enzymes, or a combination thereof.

4. The process according to claim 3, wherein the one or more than one flocculating compound is added before or during the step of introducing (step ii), or a combination thereof.

5. The process according to claim 1, wherein the pretreated cellulosic feedstock is obtained from wheat straw, oat straw, barley straw, corn stover, soybean stover, canola straw, sugar cane bagasse, switch grass, reed canary grass, cord grass, oat hulls, sugar beet pulp, or miscanthus.

6. The process according to claim 2, wherein the pretreated cellulosic feedstock is obtained from wheat straw, oat straw, barley straw, corn stover, soybean stover, canola straw, sugar cane bagasse, switch grass, reed canary grass, cord grass, oat hulls, sugar beet pulp, or miscanthus.

7. The process according to claim 4, wherein the pretreated cellulosic feedstock is obtained from wheat straw, oat straw, barley straw, corn stover, soybean stover, canola straw, sugar cane bagasse, switch grass, reed canary grass, cord grass, oat hulls, sugar beet pulp, or miscanthus.

8. The process according to claim 1, wherein the pretreated cellulosic feedstock has been subjected to pre-treatment from about 160° C. to about 280° C., and for about 3 seconds to about 30 minutes at a sulfuric acid concentration from about 0% to about 5% prior to enzymatic hydrolysis.

9. The process according to claim 6, wherein the pretreated cellulosic feedstock has been subjected to pre-treatment from about 160° C. to about 280° C., and for about 3 seconds to about 30 minutes at a sulfuric acid concentration from about 0% to about 5% prior to enzymatic hydrolysis.

10. The process according to claim 7, wherein the pretreated cellulosic feedstock has been subjected to pre-treatment from about 160° C. to about 280° C., and for about 3 seconds to about 30 minutes at a sulfuric acid concentration from about 0% to about 5% prior to enzymatic hydrolysis.

11. The process according to claim 1, wherein, in the step of adding (step iii), the cellulase enzyme is added at a dosage from about 1.0 to about 40.0 FPU per gram of cellulose.

12. The process according to claim 9, wherein, in the step of adding (step iii), the cellulase enzyme is added at a dosage from about 1.0 to about 40.0 FPU per gram of cellulose.

13. The process according to claim 10, wherein, in the step of adding (step iii), the cellulase enzyme is added at a dosage from about 1.0 to about 40.0 FPU per gram of cellulose, and the one or more than one flocculating compound is added at a dosage from about 0.1 to about 4.0 kg per tonne solids.

14. The process according to claim 1, wherein, prior to the step of removing (step iv), at least a portion of the glucose is separated from the unhydrolyzed solids by using a clarifier zone at the top of the hydrolysis reactor.

15. The process according to claim 12, wherein, prior to the step of removing (step iv), at least a portion of the glucose is separated from the unhydrolyzed solids by using a clarifier zone at the top of the hydrolysis reactor.

16. The process according to claim 13, wherein, prior to the step of removing (step iv), at least a portion of the glucose is separated from the unhydrolyzed solids by using a clarifier zone at the top of the hydrolysis reactor.

17. The process according to claim 1, wherein, in the step of removing (step iv), the aqueous stream comprising the glucose and unhydrolyzed solids is transferred to a solids-liquid separator to separate at least a portion of the glucose from the unhydrolyzed solids.

18. The process according to claim 14, wherein, in the step of removing (step iv), a stream comprising the unhydrolyzed solids is transferred to a solids-liquid separator to separate at least a portion of the glucose from the unhydrolyzed solids.

19. The process according to claim 16, wherein, in the step of removing (step iv), a stream comprising the unhydrolyzed solids is transferred to a solids-liquid separator to separate at least a portion of the glucose from the unhydrolyzed solids.

20. The process according to claim 14, wherein the unhydrolyzed solids are removed from the clarifier zone below the top of the reactor.

21. The process according to claim 15, wherein the unhydrolyzed solids are removed from the clarifier zone below the top of the reactor.

22. The process according to claim 16, wherein the unhydrolyzed solids are removed from the clarifier zone below the top of the reactor.

23. The process according to claim 1, wherein the aqueous upflowing stream further comprises cellobiose and glucose oligomers.

24. The process according to claim 12, wherein the aqueous upflowing stream further comprises cellobiose and glucose oligomers.

25. The process according to claim 13, wherein the aqueous upflowing stream further comprises cellobiose and glucose oligomers.

26. The process according to claim 1, wherein, in the step of providing (step i), the pH of the slurry is from about 4.0 to about 6.0.

27. The process according to claim 26, wherein the pH of the slurry is from about 4.5 to about 5.5.

28. The process according to claim 1, wherein, in the step of providing (step i), the temperature is from about 45° C. to about 70° C.

29. The process according to claim 28, wherein the temperature is from about 45° C. to about 65° C.

30. The process according to claim 1, wherein, in the step of adding (step iii), the cellulase enzymes are produced by *Aspergillus, Humicola, Trichoderma, Bacillus, Thermobifida*, or a combination thereof.

31. The process according to claim 4, wherein the one or more than one flocculating compound is selected from the group consisting of a cationic polymer, a non-ionic polymer, an anionic polymer, an amphoteric polymer, salts, alum, and a combination thereof.

32. The process according to claim 31, wherein the one or more than one flocculating compound is the cationic polymer.

33. The process according to claim 32, wherein the cationic polymer is a polyacrylamide.

34. The process according to claim 4, wherein the cellulase enzyme and one or more than one flocculating compound are added to the slurry together.

35. The process according to claim 4, wherein the cellulase enzyme and one or more than one flocculating compound are added to the slurry separately.

36. The process according to claim 3, wherein, in the step of providing (step i), the pH of the slurry is from about 4.0 to about 6.0.

37. The process according to claim 36, wherein the pH of the slurry is from about 4.5 to about 5.5.

38. The process according to claim 3, wherein, in the step of providing (step i), the temperature is from about 45° C. to about 70° C.

39. The process according to claim 38, wherein the temperature of the slurry is from about 45° C. to about 65° C.

40. The process according to claim 3, wherein, in the step of adding (step iii), the cellulase enzymes are produced by *Aspergillus, Humicola, Trichoderma, Bacillus, Thermobifida* or a combination thereof.

41. The process according to claim 1, wherein, in the step of providing (step i), the slurry comprises from about 5% to about 20% by weight undissolved solids, and the undissolved solids comprise from about 25% to about 70% by weight cellulose.

42. The process according to claim 1, wherein a liquid stream comprising sugar is separated from the pre-treated cellulosic feedstock of step i prior to the step of introducing (step ii).

43. The process according to claim 42, wherein a washing step is used during separation of the liquid stream from the feedstock.

44. The process according to claim 43, wherein a wash medium selected from the group consisting of water, a recycled process stream, treated effluent and a combination thereof is used during the washing step.

45. The process according to claim 1, wherein the average slurry flow velocity is between about 0.1 and about 4 feet per hour.

46. The process according to claim 1, wherein the aqueous upflowing stream comprising the glucose is removed from the top of the hydrolysis reactor.

* * * * *